United States Patent [19]

Kubersky

[11] 4,046,503
[45] Sept. 6, 1977

[54] DEVELOPER-COUPLER HAIR DYES BASED ON ALKOXY-TRIAMINO-PYRIMIDINES

[75] Inventor: Hans Peter Kubersky, Solingen, Germany

[73] Assignee: Henkel & Cie GmbH, Dusseldorf, Germany

[21] Appl. No.: 673,457

[22] Filed: Apr. 5, 1976

[30] Foreign Application Priority Data

Apr. 12, 1975  Germany ............................ 2516117

[51] Int. Cl.[2] ................................................ A61K 7/13
[52] U.S. Cl. ........................................ 8/10.2; 8/10.1; 8/10; 8/11; 8/32
[58] Field of Search ................ 260/256.4 N, 256.4 C; 96/56.5, 100; 8/10.2, 11, 32

[56] References Cited

U.S. PATENT DOCUMENTS

| | | | |
|---|---|---|---|
| 2,350,812 | 6/1944 | Peterson | 96/56.5 |
| 2,355,691 | 8/1944 | Allen et al. | 96/56.5 |
| 2,487,569 | 11/1949 | Mackey | 260/256.4 C |
| 2,584,024 | 1/1952 | Kaczka et al. | 260/256.4 C |
| 3,200,040 | 8/1965 | Lange | 8/10.2 |
| 3,359,168 | 12/1967 | Brechner et al. | 8/10.2 |
| 3,536,436 | 10/1970 | Lange | 8/10.2 |
| 3,573,272 | 3/1971 | Kaupp et al. | 260/256.4 C |

*Primary Examiner*—Albert T. Meyers
*Assistant Examiner*—Vera C. Clarke
*Attorney, Agent, or Firm*—Hammond & Littell

[57] ABSTRACT

Water-soluble substituted and unsubstituted triamino $C_{1-4}$-alkoxy pyrimidines are effective dyes for hair when oxidized in conjunction with a coupling agent. The oxidation can be performed at alkaline pH at room temperature, with air, and provides long-lasting and light-fast dyeings over a broad color range.

15 Claims, No Drawings

DEVELOPER-COUPLER HAIR DYES BASED ON ALKOXY-TRIAMINO-PYRIMIDINES

FIELD OF THE INVENTION

The present invention relates to water-soluble compositions of the developer-coupler type for the dyeing of hair. The invention includes the compositions themselves in dry and in dissolved state with and without a chemical oxidizing agent, methods for the dyeing of hair therewith, and the resulting dyed hair.

THE PRIOR ART

Of great importance for the dyeing of hair are the so-called oxidation dyestuffs because of the intense and very fast dyes which they provide. These dyes are formed by the oxidative coupling of a developer component with a coupling component. The developers customarily used are nitrogenous bases such as p-phenylenediamine derivatives, diaminopyridines, 4-aminopyrazolone derivatives, or heterocyclic hydrazones. Useful as so-called coupling components are m-phenylenediamine derivatives, phenols, naphthols, resorcinol derivatives and pyrazolones. Compositions of this type are disclosed in application Ser. No. 526,232 filed on Nov. 22, 1974, by Rose et al., now U.S. Pat. No. 4,003,699.

Good oxidation dyestuff components for the dyeing of hair should fulfill the following requirements.

They should develop the desired shades with sufficient intensity when oxidatively coupled with the respective developer component or coupling component, as the case may be. Furthermore, they have to possess an adequate capacity for being absorbed or adsorbed by human hair. In addition, they should be harmless from the toxicological and dermatological viewpoints.

As developers, it is customary to use substituted or unsubstituted p-phenylenediamines for the purpose. However, this group of compounds has the disadvantage in many instances of causing skin sensitization and subsequent severe allergies in the persons to whom these compounds are applied. The developers which have been recently proposed for avoiding these dermatological disadvantages do not always give fully satisfactory technical results when applied.

OBJECTS OF THE INVENTION

An object of the invention is to provide usable hair dye compositions of the developer-coupler type which satisfy the above requirements.

A further object of the invention is to provide compositions of this type which, when oxidized, provide dyeings over a broad color range.

A still further object is to provide compositions of the type which can be applied to hair in a customary emulsion carrier at an alkaline pH, and which develop their color without need for pH adjustment.

Another object of the present invention is to provide an oxidation dyestuff combination of a coupling component and a developer component, which is based on the water-soluble triamino $C_{1-4}$ alkoxy pyrimidines as the developer component.

These and further objects of the present invention will become apparent as the description thereof proceeds.

DESCRIPTION OF THE INVENTION

The present invention provides a composition and process for dyeing hair based upon the combination of certain triamino alkoxy pyrimidines with one or more coupling components.

It has now been found that the above-specified requirements can be fulfilled to an especially significant extent by the use of hair dyeing compositions that are based on oxidation dyestuff combinations of the developer-coupler type wherein the developer is a water-soluble 2,4,5-triamino- 6-($C_{1-4}$alkoxy) pyrimidine of the formula:

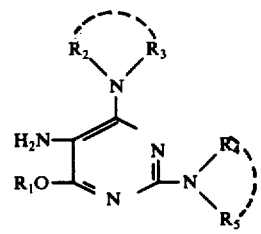

wherein $R_1$ represents $C_{1-4}$ alkyl, $R_2$-$R_5$ each represent the same or different substituents selected from the group consisting of hydrogen, $C_{1-4}$ alkyl, $C_{1-4}$ hydroxyalkyl, phenyl, $C_{1-4}$ alkylphenyl, phenyl-$C_{1-4}$ alkyl, and $C_{1-4}$ alkoxyphenyl, and wherein $R_2$ and $R_3$, or $R_4$ and $R_5$ together form divalent linking member selected from the group consisting of butylene, pentylene, azabutylene and oxabutylene, and the water-soluble salts thereof. Thus either the —$NR_2R_3$ or the —$NR_4R_5$ group, or both of these groups, can represent a mono-or di-nitrogen heterocyclic ring, which may contain an oxygen atom.

Broadly, the composition of the present invention consists essentially of the developer-coupler combination, with or without oxidizer. The composition can thus be a dry blend.

More particularly, the present invention is directed to an aqueous preparation for the dyeing of hair consisting essentially of (1) from 0.2% to 5% by weight of a developer component and a coupling component in substantially equimolar amounts, said developer component consisting essentially of (A) a triamino $C_{1-4}$ alkoxy pyrimidine of the formula:

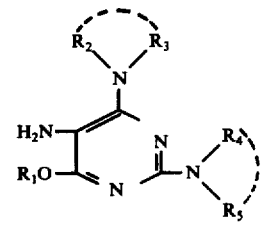

wherein $R_1$ represents $C_{1-4}$ alkyl; $R_2$, $R_3$, $R_4$, and $R_5$ each represent the same or different substituents selected from the group consisting of hydrogen $C_{1-4}$ alkyl, $C_{1-4}$ hydroxyalkyl, phenyl, $C_{1-4}$ alkylphenyl, phenyl-$C_{1-4}$ -alkyl, and $C_{1-4}$ alkoxy phenyl; and wherein $R_2$ and $R_3$, or $R_4$ and $R_5$, together form a divalent linking member selected from the group consisting of butylene, pentylene, azabutylene and oxabutylene or (B) a water-soluble acid addition salt of (A); (2) from 0% to 5% by weight of a direct dyestuff; (3) from 0% to 30% by weight of a surfactant; (4) from 0% to 25% by weight of a thickener; and (5) the balance up to 100% by weight of water.

When the compounds acccording to the invention are used as developer components, they react with the known couplers generally used in oxidation hair dyestuffs to give very intense dyeings of a variety of shades which previously heretofore could not be produced with known couplers and developers. Thus, the compounds of the invention considerably increase the possibilities for utilizing oxidation hair dyes. Furthermore, the triamino $C_{1-4}$ alkoxy pyrimidines employed in the present invention are distinguished by good water-solubility, by good storage stability, by the very satisfactory fastness of the dyeings which they provide, and by their toxicological as well as dermatological harmlessness.

The triamino $C_{1-4}$ alkoxy pyrimidines which are used as developer components according to the invention can be used either as such (i.e., in free base form) or in form of their water-soluble salts with non-toxic (i.e. dermatologically acceptable) inorganic or organic acids, such as hydrochloric acid, sulfuric acid, phosphoric acid, acetic acid, propionic acid, lactic acid or citric acid.

The preparation of many triamino $C_{1-4}$ alkoxy pyrimidines suitable for use as developer components according to the invention is already known in the literature. They can be prepared in several ways, as described more fully in the reference mentioned in the Examples and in said copending application.

Specific examples of developers suitable for use according to the invention are:
6-Methoxy-2,4,5-triamino-pyrimidine
6-Methoxy-2-methylamino-4,5-diamino-pyrimidine
6-Methoxy-2-dimethylamino-4-methylamino-5-amino-pyrimidine
6-Methoxy-2-dimethylamino-4-hydroxyethylamino-5-amino-pyrimidine
6-Methoxy-2-dimethylamino-4-anilino-5-amino-pyrimidine
6-Methoxy-2,4-bis-dimethylamino-5-amino-pyrimidine
6-Methoxy-2-benzylamino-4-5-diamino-pyrimidine
6-Methoxy-2-anisidino-4,5-diamino-pyrimidine
6-Methoxy-2,5-diamino-4-(p-dimethylamino-anilino)-pyrimidine
6-Methoxy-2-piperidino-4,5-diaminopyrimidine
6-Methoxy-2-morpholino-4,5-diamino-pyrimidine
6-Ethoxy-2,4,5-triamino-pyrimidine
6-Propoxy-2,4,5-triamino-pyrimidine
6-Butoxy-2,4,5-triamino-pyrimidine
6-Ethoxy-2-dimethylamino-4-anilino-5-amino-pyrimidine
6-Ethoxy-2-dimethylamino-4-hydroxyethylamino-5-amino-pyrimidine
6-Ethoxy-2,4-dimethylamino-5-amino-pyrimidine
6-Ethoxy-2,5-diamino-4-morpholino-pyrimidine
6-Ethoxy-2-piperidino-4,5-diamino-pyrimidine
6- Butoxy-2,4-dimethylamino-5-amino-pyrimidine
6-Butoxy-2-anisidino-4,5-diamino-pyrimidine
6-Butoxy-2-dimethylamino-4-anilino-5-amino-pyrimidine.

Specific examples of preferred coupling components to be used for the hair dyes according to the invention are as follows:
α-Naphthol
o-Cresol
m-Cresol
2,6-Dimethylphenol
2,5-Dimethylphenol
3,4-Dimethylphenol
3,5-Dimethylphenol
Pyrocatechol
Pyrogallol
1,5-Dihydroxy naphthalene
1,7-Dihydroxy naphthalene
5-Amino-2-methylphenol
Hydroquinone
2,4-Diaminoanisole
m-Toluenediamine
4-Aminophenol
Resorcinol
Resorcinol monomethyl ether (3-methoxyphenol)
m-Phenylenediamine
3-Methyl-1-phenyl-5-pyrazolone
3-Amino-1-phenyl-5-pyrazolone
1-Phenyl-3,5-dione-pyrazolidine
7-(Dimethylamino)-4-hydroxy-1-methyl-2-quinolone
1-Amino-3-(acetacetylamino)-4-nitrobenzene
1-Amino-3-(cyanoacetylamino)-4-nitrobenzene.

In the hair dye preparations according to the invention, the developer and coupling components are present in substantially equimolecular proportions. Although an equimolar amount is preferred, it is possible to use more or less of either component in the molar range of 2:1 to 1:2.

It is not necessary for the developer and the coupling components to be single chemical entities. Instead, either or both may be mixtures of compounds suitable for the respective purposes. Thus the developer component can be a mixture of several triamino $C_{1-4}$ alkoxy pyrimidines suitable for use according to the invention, and the coupling component can also consist of a mixture of one or more of the above-named coupling components.

In addition, the hair dyeing preparations according to the invention can contain admixtures of other customary developer components and, if necessary, can also contain customary direct dyestuffs in case the latter are needed for obtaining certain shades. From 0% to 5% of direct dyestuffs may be present.

As in the case of other oxidation hair dyes, the oxidative coupling (i.e., the development of the color of the dye) can be effected by atmospheric oxygen. However, it is preferred to use a chemical oxidizing agent. Suitable oxidizing agents are hydrogen peroxide or its addition products with urea, melamine and sodium borate, as well as mixtures of such hydrogen peroxide addition products with potassium peroxydisulfate.

When the triamino $C_{1-4}$ alkoxy pyrimidines according to the invention are used as developer components, they have the advantage of providing highly satisfactory hair dyeing results with atmospheric oxygen. Thus, damage to the hair by the oxidizing agent generally used for oxidative coupling can be avoided. But if bleaching and dyeing of the hair are simultaneously desired, then the concurrent use of a chemical oxidizing agent is necessary.

For use, the hair dye combinations according to the invention are incorporated into a suitable aqueous cosmetic preparation such as a cream, emulsion, gel or simple solution, and immediately before the preparation is applied to the hair, one of the above-mentioned oxidizing agents is mixed therewith. The concentration of the developer-coupler combinations in the hair dyeing preparation is between 0.2% to 5% by weight, preferably from 1% to 3% by weight.

For the preparation of creams, emulsions or gels, the dye components, separately or as dry blend, are mixed with additional ingredients customarily used in such preparations. Such additional ingredients are, for example: wetting agents or emulsifiers of the anionic or non-ionic type such as alkylbenzenesulfonates, fatty alcohol sulfates, alkylsulfonates, fatty acid alkanolamides, ethoxylated fatty alcohols; and thickeners, such as methyl cellulose, starch, higher fatty alcohols, paraffin oil, and higher fatty acids. Furthermore, perfumes and hair-conditioning and grooming agents, such as pantothenic acid and cholesterol may be included.

Effective amounts of the above-named additives are those customarily employed for this purpose. Effective amounts of wetting agents and emulsifiers range from 0.5% to 30% by weight, preferably from 1% to 15% by weight; and for thickeners, an effective amount ranges from 0.1% to 25% by weight, preferably from 1% to 15% by weight, based in each case on the total weight of the preparation. As a lower limit for the above additives, a zero percent lower limit is possible, if none of the additive is utilized.

The hair coloring preparations according to the invention can be aplied in a weakly acid medium, a neutral medium or especially, in an alkaline medium, preferably at a pH of 8 to 10 regardless whether in the medium is a solution, an emulsion, a cream, or a gel. These preparations are usually applied at a temperature in the range of 15° C. to 40° C., and are preferably applied at room temperature.

After the preparation has been allowed to remain in contact with the hair for about 30 minutes, the preparation is rinsed off and the hair is washed with a mild shampoo and dried.

When different developer and coupling components are used, the shades obtainable by use of the hair coloring preparations according to the invention have the advantage of providing extraordinary variations which extend from ash blond through dark brown and green to violet. The colors produced are excellent as far as fastness to light and washing are concerned, and possess good resistance to abrasion.

The following examples describe the invention more fully without, however, limiting it in any way.

EXAMPLE 1

The following table lists a variety of triamino $C_{1-4}$ alkoxy pyrimidines which are suitable for use in hair dye compositions of the invention. They can be prepared according to the instructions contained in the references indicated in the table.

Table 1

| Cpd. No. | Substituents | | | | | Prepared According To |
|---|---|---|---|---|---|---|
| | R1 | R2 | R3 | R4 | R5 | |
| 1 | $CH_3$ | H | H | H | H | J. Amer. Chem. Soc. 73, 2869 (1951). |
| 2 | $CH_3$ | H | $CH_3$ | $CH_3$ | $CH_3$ | By method similar to that shown in Chem. Ber. 104, 770 (1971). |
| 3 | $CH_3$ | H | $C_2H_4OH$ | $CH_3$ | $CH_3$ | |
| 4 | $CH_3$ | H | $C_6H_5$ | $CH_3$ | $CH_3$ | |
| 5 | $CH_3$ | $CH_3$ | $CH_3$ | $CH_3$ | $CH_3$ | |

EXAMPLE 2

The hair dyes according to the invention are used in the form of a cream emulsion; a series of these is prepared as follows.

In an emulsion composed of:
 10 parts by weight of fatty alcohols $C_{12}-C_{18}$ chain length 10 parts by weight of fatty alcohol sulfate (sodium salt) of $C_{12}-C_{18}$ chain length and 75 parts by weight of water were incorporated 0.01 mol each of the triamino alkoxy pyrimidines listed in Table 2 below and the coupler substances shown in Table 1 above.

The emulsions were standardized with ammonia to pH 9.5 and were made up with water to 100 parts by weight. The emulsions contained about 3% by weight of the developer-coupler combination in each instance.

EXAMPLE 3

The oxidative coupling was effected either with atmospheric oxygen or with 1% hydrogen peroxide solution as the oxidant, 10 parts by weight of hydrogen peroxide solution being added in each instance to 100 parts by weight of the emulsions.

The respective coloring creams were applied without the addition of oxidants to 90% grey, untreated human hair, and were left there for 30 minutes. After the dyeing process was completed, the hair was washed with a regular shampoo and dried. The colors obtained are shown in Table 2.

The numbers of the developer components in Table 2 correspond to the numbers in Table 1.

Table 2

| | Dye Components | | Color of Hair After Oxidation By | |
|---|---|---|---|---|
| Ex. No. | Developer | Coupler | Atmospheric Oxygen | 1% $H_2O_2$ Solution |
| 1 | 1 | m-Diamino anisol | Blue | Marine blue |
| 2 | 1 | α-Naphthol | Grey-lilac | Violet |
| 3 | 1 | 1-Phenyl-3-amino-5-pyrazolone | Pink | Pink |
| 4 | 1 | Resorcinol-monomethyl-ether (m-Methoxyphenol) | Grey-brown | Grey-brown |
| 5 | 2 | 1-Phenyl-3-amino-5-pyrazolone | Ochre-yellow | Ochre-yellow |
| 6 | 3 | α-Naphthol | Grey-violet | Violet |
| 7 | 3 | 1-Phenyl 3-amino-5-pyrazolone | Brown-orange | Light brown |
| 8 | 3 | Resorcinol-monomethylether | Red-blond | Brown-grey |
| 9 | 3 | m-Diamino anisol | Dark blue | Dark turquoise |
| 10 | 4 | α-Naphthol | Red-brown | Reddish brown |
| 11 | 4 | 1-Phenyl-3-amino-5-pyrazolone | Brown-orange | Brown-orange |
| 12 | 4 | Resorcinol-monomethyl-ether | Titian red | Titian red |
| 13 | 5 | α-Naphthol | Titian red | Titian red |
| 14 | 5 | 1-Phenyl-3-amino-5-pyrazolone | Topaz yellow | Topaz yellow |
| 15 | 5 | Resorcinol-monomethyl ether | Grey-orange | Gold blond |

It can be seen from the foregoing table that the development of color can be effected with atmospheric oxygen, and that the developer-coupling combination leads to an extremely wide variety of colors. The dyeings are characterized by fastness to light, washing and rubbing. They can be easily removed by reducing agents.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A composition of the developer-oxidizer type for the dyeing of hair, consisting essentially of, as developer, a water-soluble triamino $C_{1-4}$ alkoxy pryrimidine of the formula:

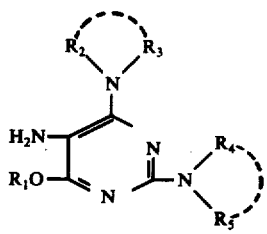

wherein $R_1$ represents $C_{1-4}$ alkyl; $R_2$, $R_3$, $R_4$ and $R_5$ each represent the same or different substituents selected from the group consisting of hydrogen, $C_{1-4}$ alkyl, $C_{1-4}$ hydroxyalkyl, phenyl, $C_{1-4}$ alkylphenyl, phenyl-$C_{1-4}$ alkyl, and $C_{1-4}$ alkoxyphenyl, and wherein $R_2$ and $R_3$, or $R_4$ and $R_5$ together form a divalent linking member selected from the group consisting of butylene, pentylene, azabutylene, and oxabutylene, or the water-soluble salts thereof, and a water-soluble coupler therefor, said developer and said coupler being present in the molar range of 2:1 to 1:2.

2. An aqueous emulsion for the dyeing of hair having a content of 0.2% to 5% by weight of the developer-coupler composition of claim 1.

3. The composition according to claim 1 wherein the developer is in the form of a water-soluble salt.

4. The emulsion according to claim 2 having a pH in the range of 8 to 10.

5. An aqueous preparation of the developer-oxidizer type for the dyeing of hair, comprising 0.2% to 5% by weight of the developer-oxidizer combination of claim 1, from 0% to 5% by weight of at least one direct dyestuff; from 0% to 30% by weight of a surfactant; from 0% to 25% by weight of a thickener, and the remainder water.

6. The composition according to claim 1 wherein the developer is 4-methoxy-2,5,6-triamino pyrimidine.

7. The composition according to claim 1 wherein the developer is 2-dimethylamino-4-methoxy-6-methylaminopyrimidine.

8. The composition according to claim 1 wherein the developer is 2-dimethylamino-6-(2-hydroxyethyl)-4-methoxypyrimidine.

9. The composition according to claim 1 wherein the developer is 6-anilino-2-dimethylamino-4-methoxypyrimidine.

10. The composition according to claim 1 wherein the developer is 2,6-di(dimethylamino)-4-methoxypyrimidine.

11. The composition according to claim 1 wherein the coupler is selected from the group consisting of m-diaminoanisol, α-naphthol, 1-phenyl-3-amino-5-pyrazolone, 3-methoxyphenol, and 3-ethoxyphenol.

12. The composition according to claim 1 wherein the developer and coupler are present in substantially equimolecular proportions, relative to each other.

13. A process for the dyeing of hair which consists essentially in contacting said hair with an effective amount of an aqueous medium containing a tinctorially effective amount of the developer-coupler composition according to claim 1 at a temperature between 15° C. and 40° C. until said hair has absorbed a tinctorial amount of said medium, and oxidizing said medium on said hair.

14. The process according to claim 13 wherein said oxidation is effected by the action of air at about room temperature.

15. The process according to claim 13 wherein said oxidation is effected by the action of hydrogen peroxide at about room temperature.

* * * * *